(12) United States Patent
Akashe et al.

(10) Patent No.: US 8,859,005 B2
(45) Date of Patent: Oct. 14, 2014

(54) ENTERIC DELIVERY OF FUNCTIONAL INGREDIENTS SUITABLE FOR HOT COMESTIBLE APPLICATIONS

(71) Applicants: Ahmad Akashe, Mundelein, IL (US); Anilkumar Ganapati Gaonkar, Buffalo Grove, IL (US)

(72) Inventors: Ahmad Akashe, Mundelein, IL (US); Anilkumar Ganapati Gaonkar, Buffalo Grove, IL (US)

(73) Assignee: Intercontinental Great Brands LLC, East Hanover, NJ (US)

( * ) Notice: Subject to any disclaimer, the term of this patent is extended or adjusted under 35 U.S.C. 154(b) by 0 days.

(21) Appl. No.: 13/692,856

(22) Filed: Dec. 3, 2012

(65) Prior Publication Data

US 2014/0154327 A1    Jun. 5, 2014

(51) Int. Cl.

| | |
|---|---|
| A61K 9/52 | (2006.01) |
| A61K 9/50 | (2006.01) |
| A61K 36/48 | (2006.01) |
| A61K 9/00 | (2006.01) |
| A23L 2/66 | (2006.01) |
| A23L 2/56 | (2006.01) |
| A23L 1/00 | (2006.01) |
| A23L 2/52 | (2006.01) |
| A23L 2/395 | (2006.01) |
| A23L 1/22 | (2006.01) |

(52) U.S. Cl.
CPC ............ *A61K 9/0002* (2013.01); *A61K 9/0095* (2013.01); *A61K 9/5042* (2013.01); *A23L 2/66* (2013.01); *A23L 2/56* (2013.01); *A61K 9/50* (2013.01); *A23L 1/0029* (2013.01); *A23L 2/52* (2013.01); *A23L 2/395* (2013.01); *A61K 9/5052* (2013.01); *A23L 1/22016* (2013.01)
USPC ........... 424/491; 424/757; 424/490; 427/2.21

(58) Field of Classification Search
None
See application file for complete search history.

(56) References Cited

U.S. PATENT DOCUMENTS

| | | |
|---|---|---|
| 2,464,204 A | 3/1949 | Baker |
| 2,727,833 A | 12/1955 | Yen et al. |
| 3,010,953 A | 11/1961 | Unger et al. |
| 3,041,289 A | 6/1962 | Katchen et al. |
| 3,116,206 A | 12/1963 | Brynko et al. |

(Continued)

FOREIGN PATENT DOCUMENTS

| | | |
|---|---|---|
| EP | 0 579 435 A1 | 1/1994 |
| EP | 0 827 997 A1 | 3/1998 |

(Continued)

OTHER PUBLICATIONS

Lee et al., "Characteristics of Sodium Caseinate- and Soy Protein Isolate-Stabilized Emulsion-Gels Formed by Microbial Transglutaminase," Journal of Food Science, vol. 71, Nr. 6; 2006; p. C352-C357.*

(Continued)

*Primary Examiner* — Tracy Vivlemore
*Assistant Examiner* — Monica Shin
(74) *Attorney, Agent, or Firm* — Fitch, Even, Tabin & Flannery LLP (57) ABSTRACT

A microencapsulated enteric matrix composition and method for manufacture are provided. The microencapsulated enteric composition includes enteric material, such as sodium caseinate and soy protein, and a functional ingredient contained therein in a core. Further, the composition includes a first coating including zein and the second, outer coating including ethylcellulose. The microencapsulated enteric composition may be suitable for use in hot comestibles.

16 Claims, 5 Drawing Sheets

(56) References Cited

U.S. PATENT DOCUMENTS

| | | | |
|---|---|---|---|
| 3,869,406 A | 3/1975 | Matsukawa et al. |
| 3,956,172 A | 5/1976 | Saeki et al. |
| 4,432,966 A | 2/1984 | Zeitoun et al. |
| 4,515,769 A | 5/1985 | Merritt et al. |
| 4,518,458 A | 5/1985 | Greenfield et al. |
| 4,601,863 A | 7/1986 | Shioi et al. |
| 4,702,798 A | 10/1987 | Bonanno |
| 4,778,781 A | 10/1988 | Washizu et al. |
| 4,895,725 A | 1/1990 | Kantor et al. |
| 4,936,916 A | 6/1990 | Shinmitsu et al. |
| 5,051,304 A | 9/1991 | David et al. |
| 5,051,305 A | 9/1991 | Whitaker, Sr. |
| 5,146,758 A | 9/1992 | Herman |
| 5,160,742 A | 11/1992 | Mazer et al. |
| 5,164,210 A | 11/1992 | Campbell et al. |
| 5,418,010 A * | 5/1995 | Janda et al. ............. 427/213.31 |
| 5,480,656 A | 1/1996 | Okada et al. |
| 5,601,760 A | 2/1997 | Rosenberg |
| 5,679,377 A | 10/1997 | Bernstein et al. |
| 5,686,092 A | 11/1997 | Lewis |
| 5,879,541 A | 3/1999 | Parkinson |
| 5,882,715 A | 3/1999 | Nielsen et al. |
| 5,958,388 A | 9/1999 | Franks |
| 6,143,170 A | 11/2000 | Briggs et al. |
| 6,608,017 B1 | 8/2003 | Dihora et al. |
| 6,632,451 B2 | 10/2003 | Penhasi et al. |
| 6,653,288 B1 | 11/2003 | Beuvry et al. |
| 6,770,285 B2 | 8/2004 | Keenan et al. |
| 6,893,662 B2 | 5/2005 | Dittmar et al. |
| 6,921,539 B2 | 7/2005 | Ninkov |
| 6,923,988 B2 | 8/2005 | Patel et al. |
| 6,929,810 B2 | 8/2005 | Purohit et al. |
| 6,929,814 B2 | 8/2005 | Bouwmeesters et al. |
| 7,067,153 B2 | 6/2006 | Grisoni |
| 7,182,959 B2 | 2/2007 | Martani |
| 7,192,542 B2 | 3/2007 | Ugazio |
| 7,250,185 B2 | 7/2007 | Dowdle et al. |
| 7,279,495 B2 | 10/2007 | Ducray et al. |
| 7,338,928 B2 | 3/2008 | Lau et al. |
| 7,425,342 B2 | 9/2008 | Kannar |
| 7,427,407 B2 | 9/2008 | Kume et al. |
| 7,491,406 B2 | 2/2009 | Leung et al. |
| 7,541,155 B2 | 6/2009 | Enan |
| 7,585,538 B2 | 9/2009 | Mangos et al. |
| 7,622,269 B2 | 11/2009 | Enan |
| 8,057,784 B2 | 11/2011 | Witteveen et al. |
| 2002/0055537 A1 | 5/2002 | Gerlach et al. |
| 2002/0173522 A1 | 11/2002 | Redmon et al. |
| 2002/0193452 A1 | 12/2002 | Brocker et al. |
| 2003/0082272 A1 | 5/2003 | Bouwmeesters et al. |
| 2003/0175403 A1 | 9/2003 | Gurin |
| 2003/0180369 A1 | 9/2003 | Grisoni |
| 2003/0203848 A1 | 10/2003 | Vertesy et al. |
| 2003/0225003 A1 | 12/2003 | Ninkov |
| 2003/0228369 A1 | 12/2003 | Kuhrts |
| 2004/0109894 A1 | 6/2004 | Shefer et al. |
| 2004/0191366 A1 | 9/2004 | Mangos et al. |
| 2004/0195711 A1 | 10/2004 | Hayashi et al. |
| 2004/0266888 A1 | 12/2004 | Ninkov |
| 2005/0014827 A1 | 1/2005 | Schur |
| 2005/0054682 A1 | 3/2005 | Phillips |
| 2005/0079138 A1 | 4/2005 | Chickering, III et al. |
| 2005/0100640 A1 | 5/2005 | Pearce |
| 2005/0123603 A1 | 6/2005 | Dalland et al. |
| 2005/0181053 A1 | 8/2005 | Dittmar |
| 2005/0181059 A1 | 8/2005 | Jacob et al. |
| 2005/0200035 A1 | 9/2005 | Dobbs |
| 2005/0287276 A1 | 12/2005 | Lavoie et al. |
| 2006/0134282 A1 | 6/2006 | Mellema |
| 2006/0147503 A1 | 7/2006 | Floyd |
| 2006/0240108 A1 | 10/2006 | Bernard |
| 2006/0280795 A1 | 12/2006 | Penhasi et al. |
| 2007/0042045 A1 | 2/2007 | Lizio et al. |
| 2007/0072944 A1 | 3/2007 | Gauvry et al. |
| 2007/0134332 A1 | 6/2007 | Turnell et al. |
| 2007/0141147 A1 | 6/2007 | Heil et al. |
| 2007/0145326 A1 | 6/2007 | Joseph et al. |
| 2007/0148198 A1 | 6/2007 | Joseph et al. |
| 2007/0190080 A1 | 8/2007 | Friedman |
| 2007/0218125 A1 | 9/2007 | Head et al. |
| 2008/0020078 A1 | 1/2008 | Enan |
| 2008/0029625 A1 | 2/2008 | Talton |
| 2008/0038362 A1 | 2/2008 | Park et al. |
| 2008/0081070 A1 | 4/2008 | Wilson et al. |
| 2008/0125461 A1 | 5/2008 | Barberich |
| 2008/0145462 A1 | 6/2008 | Enan |
| 2008/0193531 A1 | 8/2008 | Hermelin et al. |
| 2008/0207766 A1 | 8/2008 | Devane |
| 2008/0226623 A1 | 9/2008 | Margolin et al. |
| 2008/0226649 A1 | 9/2008 | Schetter et al. |
| 2008/0226684 A1 | 9/2008 | Peppas |
| 2008/0255498 A1 | 10/2008 | Houle |
| 2008/0260819 A1 | 10/2008 | Fleming et al. |
| 2008/0299087 A1 | 12/2008 | Tseng et al. |
| 2009/0186096 A1 | 7/2009 | Kritzman et al. |
| 2009/0215892 A1 | 8/2009 | Nahab et al. |
| 2010/0015224 A1 | 1/2010 | Singh et al. |
| 2010/0129446 A1 | 5/2010 | Liu et al. |
| 2010/0307542 A1 | 12/2010 | Akashe et al. |
| 2010/0310666 A1 | 12/2010 | Gaonkar et al. |
| 2010/0310726 A1 | 12/2010 | Akashe et al. |
| 2011/0008471 A1 | 1/2011 | Enan |
| 2011/0020520 A1 | 1/2011 | Van Lengerich et al. |
| 2011/0124502 A1 | 5/2011 | Enan |
| 2011/0159103 A1 * | 6/2011 | Akashe et al. ............... 424/491 |
| 2012/0251641 A1 | 10/2012 | Enan et al. |

FOREIGN PATENT DOCUMENTS

| | | |
|---|---|---|
| EP | 1 396 551 A1 | 3/2004 |
| EP | 1 721 605 A1 | 11/2006 |
| JP | 52-152876 A | 12/1977 |
| JP | S63-197540 A | 8/1988 |
| JP | H02-103289 A | 4/1990 |
| JP | 04-330934 A | 11/1992 |
| JP | 05-017338 A | 1/1993 |
| JP | 08-026930 A | 1/1996 |
| JP | 10-273650 A | 10/1998 |
| JP | 2003-012526 A | 1/2003 |
| JP | 2004-018443 A | 1/2004 |
| JP | 2007-177129 A | 7/2007 |
| JP | 2008-013529 A | 1/2008 |
| RU | 2 098 121 C1 | 12/1997 |
| RU | 2 332 257 C2 | 3/2006 |
| WO | 82/02496 A1 | 8/1982 |
| WO | 84/03201 A1 | 8/1984 |
| WO | 93/19622 A2 | 10/1993 |
| WO | 00/36924 A1 | 6/2000 |
| WO | 02/38181 A2 | 5/2002 |
| WO | 03/097015 A1 | 11/2003 |
| WO | 2005/082320 A1 | 9/2005 |
| WO | 2006/093838 A1 | 9/2006 |
| WO | 2007/044437 A2 | 4/2007 |
| WO | 2007/094000 A2 | 8/2007 |
| WO | 2008/003996 A1 | 1/2008 |
| WO | 2009/117623 A2 | 9/2009 |

OTHER PUBLICATIONS

Colorcon, "Ethocel™ Premium Ethylcellulose Polymers," <http://www.colorcon.com/literature/marketing/mr/Extended%20Release/ETHOCEL/Chinese/730%20Colorcon%20Ethocel2%20w-new%20logo-09.03.09.pdf>; © Colorcon, 2009; p. 1-2.*

Dowwolff, "Ethylcellulose," <http://www.dow.com/dowwolff/en/industrial_solutions/polymers/ethylcellulose/>; published Sep. 5, 2012; p. 1.*

C. L. Kruger and S.W. Mann, Safety evaluation of functional ingredients, Food and Chemical Toxicology, vol. 41, No. 6, Jan. 1, 2003, pp. 793-805, XP009144244, Pergamon, Great Britain.

Claudia S. Leopold and David R. Friend, "In vitro study for the assessment of poly(L-aspartic acid) as a drug carrier for colon-specific drug delivery," International Journal of Pharmaceutics, vol. 126, 1995, pp. 139-145.

(56) References Cited

OTHER PUBLICATIONS

European Patent Office Extended European Search Report for European Application No. 10251026.0 dated Aug. 30, 2010 (7 pages).
European Patent Office Extended European Search Report for European Application 10251044.3 dated Feb. 21, 2011 (6 pages).
Intellectual Property Office of New Zealand Examination Report dated Jun. 1, 2010 for New Zealand Application 585723, 3 pages.
Intellectual Property Office of New Zealand Examination Report dated Jun. 2, 2010 for New Zealand Application 585724, 3 pages.
Intellectual Property Office of New Zealand Examination Report dated Jun. 2, 2010 for New Zealand Application 585725, 3 pages.
L. R. Salgueiro et al., "Chemical Composition and Antifungal Activity of the Essential Oil of Origanum virens on Candida Species," Planta Med, vol. 69, 2003, pp. 871-874.
M. A. Del Nobile et al., Antimicrobial efficacy and release kinetics of thymol from zein films, Journal of Food Engineering, vol. 89, No. 1, Nov. 1, 2008, pp. 57-63, XP022704837, Barking, Essex, Great Britain.
Nicholas Parris et al., Encapsulation of Essential Oils in Zein Nanospherical Particles, Journal of Agricultural and Food Chemistry, vol. 53, Jun. 15, 2005, pp. 4788-4792, XP-002599360, American Chemical Society, United States of America.
Parag Kolhe et al., "Preparation, cellular transport, and activity of polyamidoamine-based dendritic nanodevices with a high drug payload," Biomaterials, vol. 27, 2006, pp. 660-669.
Pavan Muttil et al., "Inhalable microparticles containing large payload of ani-tuberculosis drugs," European Journal of Pharmaceutical Sciences, vol. 32, 2007, pp. 140-150.
Sunil A. Agnihotri et al., "Recent advances on chitosan-based micro- and nanoparticles in drug delivery," Journal of Controlled Release, vol. 100, 2004, pp. 5-28.
PCT International Searching Authority International Search Report and Written Opinion for International Application No. PCT/US2011/065828 dated May 23, 2012, 11 pages.
Max S. Dunn and Howard B. Lewis, "The Action of Nitrous Acid on Casein," Journal of Biological Chemistry, vol. 49, 1921, pp. 327-341.
L. K. Ramachandran and W. B. McConnell, "The Action of Sulphuric Acid on Gliadin: With Special Reference to the N-Peptidyl→O-Peptidyl Bond Rearrangement," Canadian Journal of Chemistry, vol. 33, 1955, pp. 1638-1648.
R. M. Allison et al., "Notes on a deamination method proposed for determining 'chemically available lysine' of proteins," British Journal of Nutrition, vol. 29, 1973, pp. 51-55.
J. W. Paulis, "Disulfide Structures of Zein Proteins from Corn Endosperm," Cereal Chemistry, vol. 58, No. 6, 1981, pp. 542-546.
Microencapsulation of Food Ingredients, Edited by Per Vilstrup, Leatherhead Food RA Publishing, 2001, pp. 5-6.
LinShu Liu et al., "Pectin/Zein Beads for Potential Colon-Specific Drug Delivery: Synthesis and in Vitro Evaluation," 2006a, vol. 13, pp. 417-423.
Ain Raal et al., "Content and composition of the essential oil of *Thymus serpyllum* L. growing wild in Estonia," Medicina (Kaunas), 2004, 40(8), 795-800.
SIDS Initial Assessment Report for SIAM 14 dated Mar. 2002, Linalyl Acetate CAS No. 115-95-7, http://www.chem.unep.ch/irptc/sids/OECDSIDS/115957, 57 pages.
Wikipedia entry for Lavender oil, 2013, http://en.wikipedia.org/wiki/Lavender_oil, 5 pages.

* cited by examiner

ENTERIC DELIVERY OF FUNCTIONAL INGREDIENTS SUITABLE FOR HOT COMESTIBLE APPLICATIONS

FIELD

The present application relates to microencapsulated materials, such as for use in hot foods and beverages, and methods for their manufacture. More particularly, the microencapsulated materials include functional ingredients in an enteric matrix further coated with enteric materials which are suitable for use in hot foods and beverages and which release functional ingredients in a user's intestines.

BACKGROUND

Enteric delivery of functional materials in food applications has been limited. Enteric delivery systems are commonly utilized when the functional materials or medicaments are known to be sensitive to certain conditions such that they become less effective or if the functional materials cause problems for the user, such as stomach problems with aspirin. Further, enteric delivery systems are commonly utilized when the functional materials or medicaments are known to be sensitive to low pH or have undesirable flavor and/or taste characteristics which cannot be effectively masked by other methods.

Generally, enteric delivery, as most common in pharmaceutical practice, is accomplished by coating tablets and gel capsules. However, those particular delivery methods are not well suited for food applications. In particular, neither tablets nor capsules are sized to be integrated into most existing food products.

An alternative process for enteric delivery is microencapsulation. However, one issue with microencapsulation is the recovery rate, or microencapsulation efficiency of the process. Generally, a certain significant percentage of the material to be microencapsulated is not captured. The uncaptured material may be recovered for reuse, recycled, or a percentage of the uncaptured material remains adhered to the outer surface of the microencapsulated particulates.

In the situation where uncaptured material remains adhered to the microencapsulated particles, the product tends to have a taste profile associated with the uncaptured material, which is often undesirable. This is particularly true when the uncaptured material includes oxidizable triglycerides such as unsaturated and polyunsaturated lipids, oxidizable flavors and essential oils, or other organic compounds that may naturally have strong undesirable taste and/or flavor. For example, functional ingredients, such as essential oils, are known to possess health benefits and protect against intestinal parasites. However, one limitation of incorporating essential oils into foods and beverages is their strong pungent smell and taste.

Further, there have been a number of previous attempts at developing enteric delivery of functional ingredients, such as essential oils, for use at ambient and cold temperature. In one form, these materials may be provided in the form of powdered beverages. However, such systems fail to provide protection and taste masking at a temperature above about 35° C. as the enteric delivery system fails at elevated temperatures. For example, as the powdered beverage is hydrated and heated to form a hot beverage, the enteric materials used to contain the functional ingredients degrade, thereby releasing the functional ingredients prematurely, such as when the beverage is being prepared and/or when the beverage is introduced into a user's mouth. In this regard, the user may perceive any undesirable taste profiles of the functional ingredient. Moreover, if the functional ingredient is susceptible to degradation, such as in the user's stomach, the functional ingredient may not provide sufficient delivery of the desired beneficial effects.

SUMMARY

It has unexpectedly found that microencapsulated materials may be manufactured which are suitable for use in higher temperature foods and beverages, while still providing acceptable enteric delivery properties. For example, functional ingredients, such as essential oils may be microencapsulated into an enteric matrix. Further, a coating of an enteric material may be applied.

In one form, a microencapsulated composition for use in hot foods and beverages is provided. The composition includes a core, a first coating and a second coating. The core includes a functional ingredient and an enteric material to microencapsulate the functional ingredient within a matrix of the enteric material. The enteric material includes sodium caseinate and soy protein. The first coating substantially surrounds the core and includes zein. The second coating substantially surrounds the first coating and includes ethylcellulose.

According to one form, the enteric material consists essentially of sodium caseinate and soy protein.

In accordance with one form, the core includes about 1 to about 80 wt. % of sodium caseinate and about 1 to about 80 wt. % soy protein, each on a dry basis of the core ingredients.

In one form, the composition has a moisture content of less than about 5 wt. %.

According to one form, the composition comprises about 1 to about 70 wt. % sodium caseinate and about 1 to about 70 wt. % soy protein, each on a dry basis of the total composition ingredients.

In accordance with one form, the composition comprises about 1 to about 19 wt. % zein on a dry basis of the total composition ingredients.

In one form, the composition comprises about 1 to about 19 wt. % ethylcellulose on a dry basis of the total composition ingredients.

According to one form, the functional ingredient comprises essential oils.

In accordance with one form, a method of forming a multi-coated precipitate of a microencapsulated composition for use in hot foods and beverages is provided. The method includes the steps of: agitating a combination of water and an enteric material at an appropriate pH to solubilize the enteric material, the enteric material including soy protein and sodium caseinate; adding a functional ingredient to the combination; mixing the combination and the functional ingredient to create an emulsion; titrating the emulsion with a cross-linking or precipitating agent in an amount effective to form a particulate precipitate including a matrix of the enteric material microencapsulating the functional ingredient; separating and drying the particulates; coating the particulate precipitate with a first coating including zein to form a coated particulate precipitate; and coating the coated precipitate with a second coating including ethylcellulose to form a multi-coated particulate precipitate.

DETAILED DESCRIPTION

Disclosed is a microencapsulated composition including a functional ingredient and a method for manufacture. Generally, the composition includes one or more enteric materials as well as one or more coatings that can be used in combination to delay the release of the functional ingredient prior to dissolution in the intestine. Such a combination of features may be suitable for use in a comestible which can be prepared as a hot comestible, such as a hot beverage. As used herein, the term "hot comestible" includes foods, drinks and the like which are prepared and/or served at a temperature in a range of about 25 to about 80° C. In one form, the temperature range is from about 40 to about 70° C.

Generally, it should be understood that the term "matrix" refers to a type of encapsulation that is somewhat different from traditional "true encapsulation" which has a single functional material coated by the encapsulating material. Matrix encapsulation is generally directed to a three dimensional material, which may be spherical, semi-spherical and the like, with multiple active particulates, liquids and/or solids distributed and/or embedded throughout the matrix particle. For example, in one form, the matrix includes a plurality of oil droplets are dispersed throughout the matrix material. Therefore, the matrix particle may include a plurality of oil droplets dispersed in the matrix material. In one form, the matrix may stabilize and/or protect the functional ingredients within. The matrix particle may then be encapsulated with one or more coatings.

Figure 1:
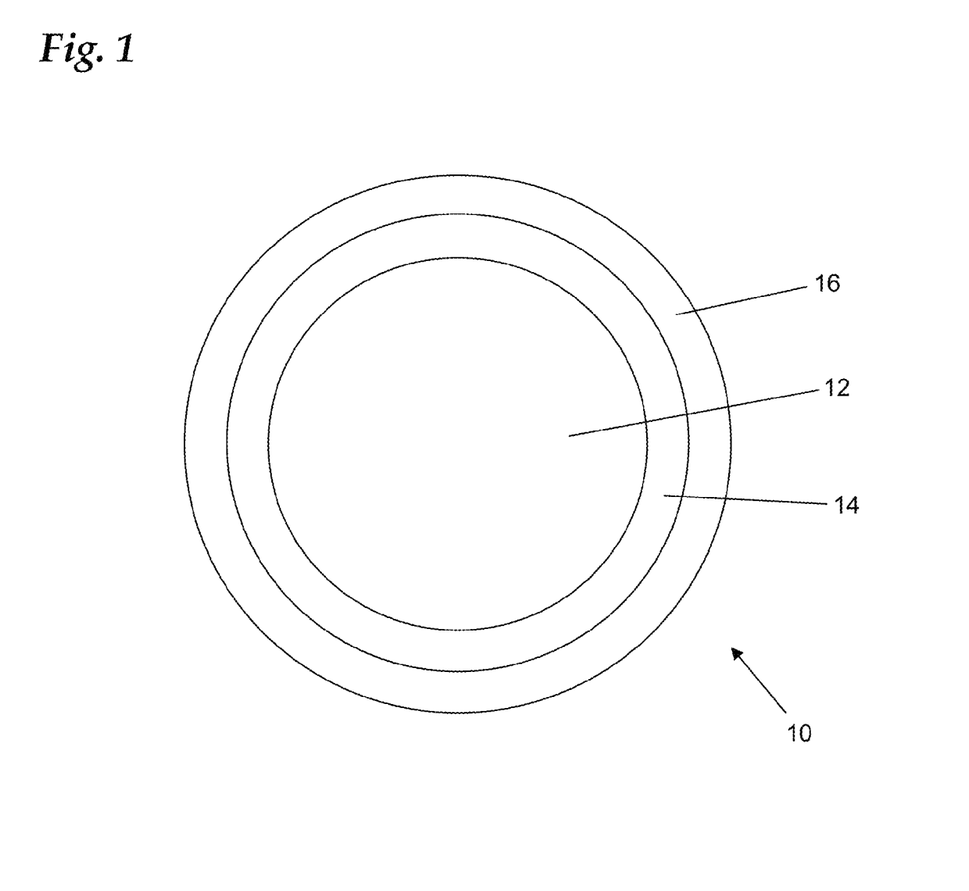
FIG. 1 is a diagrammatic representation of an enteric material including a core and a plurality of coatings.

As shown in FIG. 1, one form of a microencapsulated material 10 is shown. In one form, the microencapsulated material 10 includes a core 12, a first coating 14 and a second coating 16. It should be noted that the microencapsulated material 10 may include any number of coatings suitable for providing a composition which is suitable for use in hot comestibles. Further, it should be noted that the microencapsulated material 10 may take a variety of shapes, including irregular shapes.

The core 12 generally may include a number of different components, such as a functional ingredient, a non-active carrier, one or more enteric materials and the like. According to one form, the selection of materials for the core 12 may be such that the core 12, by itself, has enteric properties. For example, the core 12 may include functional ingredients such as essential oils, non-active carriers such as lipids and enteric materials such as soy protein and sodium caseinate. According to one form, the core includes about 1 to about 80 wt. % soy protein and about 1 to about 80 wt. % sodium caseinate, both on a dry weight basis of the core ingredients. In another form, the core includes about 20-60 wt. % of each of the soy protein and sodium caseinate. In one form, soy protein may be provided in an amount of about 1 to about 70 wt. % relative to the overall microencapsulated material 10 and the sodium caseinate may be provided in an amount of about 1 to about 70 wt. % relative to the overall microencapsulated material 10. In another form, the overall microencapsulated material 10 may include 10-60 wt. % of each of the soy protein and sodium caseinate. Further, the core 12 may include a ratio of about 1:2.5 to about 1:3.5 of the functional ingredient to the combination of the soy protein and sodium caseinate.

Other materials may be included in the core 12 as will be discussed below in more detail and as found in the examples provided herein. The core 12 may take a variety of forms, including, but not limited to core capsules. In one form, the core 12 may have enteric properties, but may not provide sufficient protection for the core 12, such as when used in a hot comestible.

The first coating 14 may include a variety of different materials, including, but not limited, to enteric materials. For example, in one form, the first coating 14 includes zein. According to another form, the first coating 14 includes an alcohol-based zein (which generally refers to a binary solvent of alcohol and water). The first coating 14 may be provided in a variety of amounts and thicknesses as desired. For example, in one form, the first coating 14 includes about 1 to about 25 wt. % zein on a dry basis of the total composition. In another form, the first coating 14 includes zein such that zein is provided in an amount of about 5 to about 19 wt. % relative to the total microencapsulated material 10. It should be noted that other materials may be included in the first coating 14 as will be described below in more detail and as found in the examples provided herein.

The second coating 16 may also include a variety of different materials, including, but not limited to enteric materials. For example, in one form, the second coating 14 includes ethylcellulose. The second coating 16 may be provided in a variety of amounts and thicknesses as desired. For example, in one form, the second coating 16 includes about 1 to about 25 wt. % ethylcellulose on a dry weight basis of the total composition. In another form, the second coating 16 includes ethylcellulose such that ethylcellulose is provide in an amount of about 5 to about 19 wt. % relative to the microencapsulated material 10. It should be noted that other materials may be included in the second coating 16 as will be described below in more detail and as found in the examples provided herein. In one form, the second coating has a melt point of greater than about 100° C.

In one form, the composition may be composed of core capsules containing proteins such as sodium caseinate and soy prepared at their isoelectric point. The core microcapsules may then be coated with a unique combination of food grade, enteric polymers. According to one form, the first coating is prepared from a binary solvent (alcohol/water) based zein solution, and the second coating is also prepared from a binary solvent (alcohol/water) based ethylcellulose (EC). It is believed that the combination of the two coatings with the core materials may be used to provide improved taste/flavor masking, especially when used in hot comestibles. For example, ethylcellulose generally may be used as a very good moisture barrier as it is relatively insoluble in water, and has a high glass transition temperature (Tg) of greater than about 100° C. In addition to the excellent moisture barrier and high Tg, ethylcellulose may also function to provide a delayed release of the functional ingredient. In other words, ethylcellulose may be provided as the second coating, such as an outermost coating, to thereby provide thermal protection and also protection when the comestible is being prepared due to its solubility properties.

Zein may be used as the first coating, which in an inner coating that is otherwise protected by ethylcellulose as the second coating. The zein may be used to provide a more controlled enteric release of the functional ingredient at the desired pH when ingested by the user.

As used herein, "functional ingredient" generally refers to any non-polar, water insoluble or immiscible liquid, such as essential oils, functional oils, oil solubles and any other functional material.

The functional ingredient can include any mixture of hydrophobic liquids and solids, such as solids mixed or combined therewith or dissolved or solubilized therein. As an example, functional ingredients can be selected to include materials which are desired to be released in the small intestine rather than the stomach due to pH sensitivity. As an example, the functional ingredient can include compositions described in U.S. Patent Publication No. 2008/0145462 to Enan. For instance, the functional ingredient includes about 25 to about 35% by weight para-cymene, about 1 to about 10% by weight linalool, about 1 to about 10% by weight alpha-pinene, about 35 to about 45% by weight thymol, and about 20 to about 30% by weight soybean oil.

In particular, the functional ingredient described herein can include an essential oil blend which possesses anti-parasitic properties. In one embodiment, the essential oil blend is organic compounds blended with food grade oil, i.e. soybean oil. Further, the organic compounds can include thymol and linalool. In a further embodiment, the organic compounds include alpha-pinene and para-cymene. One exemplary blend of an essential oil includes, by weight, about 17.5 percent soybean oil, about 8 percent alpha-pinene (liquid), about 44 percent para-cymene (liquid), about 5 percent linalool (liquid) and about 25.5 percent thymol (crystal). In another embodiment, the functional ingredient may also include modified forms of the hydrophobic liquid, as described in provisional Patent Application Ser. No. 61/422,439, filed Dec. 13, 2010, which is incorporated herein in its entirety by reference. In yet another embodiment, the hydrophobic liquid includes esters, such as esters of linalool and thymol, as described in application Ser. No. 12/479,444, filed Jun. 5, 2009, which is incorporated herein in its entirety by reference. Another exemplary form includes about 10 wt. % para-cymene, 5 wt. % alpha-pinene, 15 wt. % linalyl acetate, and about 70 wt. % thymyl octanoate.

The functional ingredient can include a portion which is modified, such as by esterification, and can comprise from about 1 to about 99 percent of the functional ingredient by weight. In some approaches, the modified functional ingredient can include from at least about 10 percent of the functional ingredient by weight and, in other approaches, about 30 percent by weight. In another embodiment, the modified functional ingredient can include from about 25 to about 65 percent of the functional ingredient by weight.

In one embodiment, the blend of non-active carrier and functional ingredient can include, by weight, about 15 to about 30 percent canola oil, about 1 to about 10 percent alpha pinene, about 5 to about 25 percent para-cymene, about 5 to about 20 percent linalyl ester and about 20 to about 60 percent thymyl ester. In other approaches, the blend of non-active carrier and functional ingredient can include, by weight, about 20 to about 25 percent canola oil, about 2 to about 7 percent alpha pinene, about 10 to about 20 percent para-cymene, about 7 to about 15 percent linalyl ester and about 35 to about 50 percent thymyl ester.

By one approach, the selected esterified form of the functional ingredient may have increased functionality due to an increased rate of hydrolysis over the parent form after ingestion and release from the enteric matrix in an intestinal tract. Esters may be obtained from natural sources or synthesized using any suitable chemical or biochemical reactions between functional ingredients, such as thymol and linalool, and organic or inorganic oxoacids that yield esters. Suitable oxoacids may include carboxylic acid, amino acids, phosphoric acid, sulfuric acid, and nitric acid. The hydroxyl group can be derived from a homogenous source (e.g., thymol) or mixed source (thymol and linalool). Exemplary monocarboxylic acids include, but are not limited to, acetic, propionic, butyric, pentanoic, hexanoic, octanois, decanoic, stearic, lactic, cinnamic, pyruvic, benzoic, and gluconic acids. Exemplary dicarboxylic acids include, but are not limited to, oxalic, malonic, maleic, fumaric, tartaric, succinic, glutaric, glucaric, adipic, pimelic, suberic, azelaic, and sebacic acids. Exemplary tricarboxylic acids, include, but are not limited to, citric and isocitric acids. Other exemplary esters that may be formed by reactions of terpenes with oxoacids include dithymol succinate, dithymol adipate, and dithymol sebacate.

In another form, the modified functional ingredient can include an ester formed, regardless of chemical or biochemical reaction approach for its preparation, between terpene esters and other esters. In particular, the functional group can be formed using transesterification. For example, the functional group can include an ester formed by reacting thymol acetate with methyl octanoate or tripalmitin.

Alternatively, it is anticipated that the functional ingredient can include other modified compounds. In one form, the modified functional group can include any glycoside formed by chemical or biochemical reaction between the hydroxyl group(s) of a terpene and a single sugar group (monosaccharide) or several sugar groups (oligosaccharide). For example, thymol and/or linalool glycosides can be the modified functional ingredient. The sugar group can include any glycoside with the glycone portion composed of mono, di, tri, and/or polysaccharides of any kind and the aglycone portion being any hydroxy-terpene (e.g., thymol, linalool). The sugar group can also include reducing sugars and/or non-reducing sugars. Exemplary sugars include, but are not limited to, glucose, fructose, galactose, ribose, sucrose, mannose, maltose, lactose, and cellobiose.

In another form, it is anticipated that the functional group can include any ionic or nonionic salt or complex formed involving a hydroxy-terpene and another chemical species. For example, thymol and linalool salts or complexes can be the modified functional ingredient. One example may be sodium and/or potassium salts. In another form, the modified functional ingredient may include thymol salts that do not have fixed stoichiometries. For example, thymol salts may be prepared as partial or mixed salts having different ratios of cations and thymol comprising one or more specific cations (Na+, K+, Mg++, etc.) to prepare solid complexes. The solidified complexes may or may not be obtained in crystalline form. The salt or complex may be formed by any suitable method, but in some cases is formed by a chemical reaction or association between one or more hydroxy-terpene and one or more alkaline reagent. Exemplary alkaline reagents may include, but are not limited to, alkaline hydroxide, oxide, or carbonate. The salt or complex can include any alkali metal, alkaline earth metal, or transition metal element, or combination thereof. Suitable salts or complex for use in foods may include those formed from sodium, potassium, lithium, calcium, magnesium, iron, manganese, zinc, and aluminum. Other exemplary salts include any mono, di, or trivalent salt of thymol, including sodium thymolate (e.g., sodium thymoxide) and any mono, di, or trivalent salt of phenol, including calcium phenoxide.

Furthermore, the functional ingredient may include various forms of modification that are combined. For example, a portion of the modified functional ingredient composition may include one or more of salts, glycosides, complexes and esterified forms of one or more essential oils.

Modifications to the functional ingredient may include a variety of forms that modify the perceived taste and/or organoleptic properties of the functional ingredient. For example, the modification may cause a change to the flavor and/or taste threshold of the functional ingredient. In one form, the modification causes a change to the volatility and/or vapor pressure of the modified functional ingredient with respect to the non-modified, parent form of the functional ingredient. In particular, the organoleptic properties of the modified form may include a higher taste threshold. As a result, in some cases a modified functional ingredient on the surface of the enteric matrix may produce a less undesirable flavor profile than the presence of unmodified functional ingredients. Further, the modifications may include salt, glycoside, complex and/or esterification of the functional ingredient.

When ingested and released in the intestinal tract, the modified form of the functional ingredient reverts back, at least in part, into the parent form and provides the same functional benefits as if the parent functional ingredient was microencapsulated and consumed. In one form, the modified functional ingredient hydrolyzes from the modified form back into the parent, non-modified form of the functional ingredient during digestion.

In some approaches, the functional ingredient described herein can include compounds which possess functional properties, such as anti-parasitic, anti-protozoan, and anti-fungal. In one embodiment, the organic compounds further include alpha-pinene and para-cymene.

Other suitable examples of a materials which may be included in the core include unsaturated and polyunsaturated OMEGA 3, other unsaturated and polyunsaturated lipids or fatty acids and triglycerides thereof, beta-carotene, and oil soluble vitamins, stomach irritants, or any other hydrophobic materials that are either sensitive to acidic pH conditions or impart strong undesirable taste.

Due to the low water solubility and/or increased hydrophobicity, an ester may have higher microencapsulation efficiency, such as described above, than non-esterified parent compounds, such as thymol and linalool. Preferably, the efficiency increases about 50 to about 200 percent over the efficiency observed when using non-esterified functional ingredients, more preferably about 100 to about 150 percent. Further, esters have a higher olfactory perception threshold than the parent compounds, such that amount of esters necessary to be perceived is more than the amount of non-esterified thymol and linalool.

Figure 2:
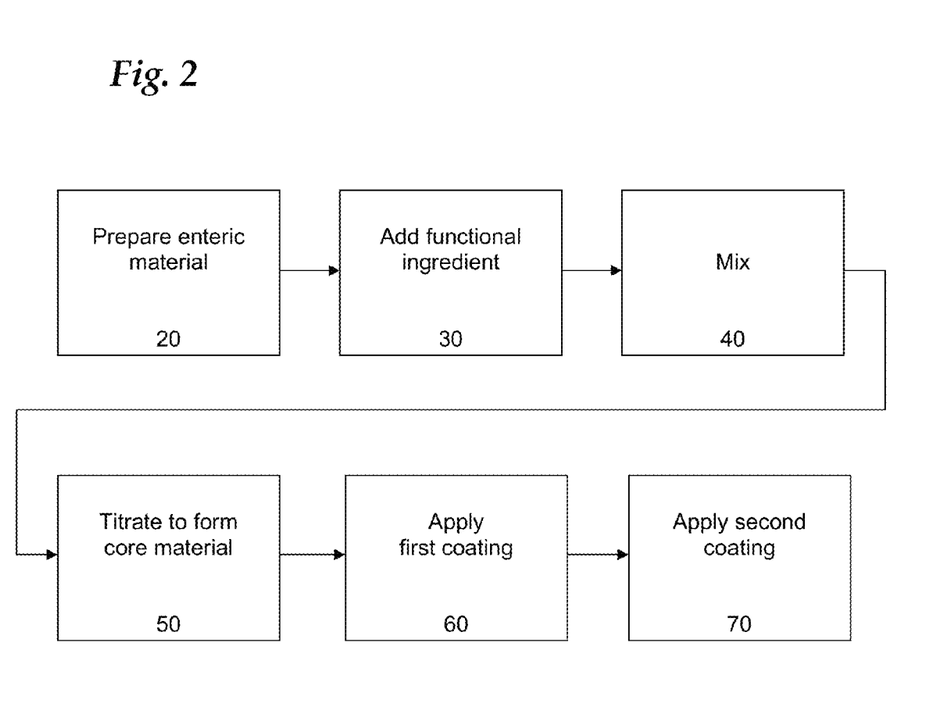
FIG. 2 is a process flow diagram illustrating one form of a method for producing enteric materials.

Methods are provided for microencapsulating one or more function ingredients therein. One method for microencapsulating a functional ingredient is generally described in FIG. 2. As shown in FIG. 2, water, an enteric material and optionally an emulsifier are subjected to agitation until the enteric material and emulsifier are combined with the water to form a solution, such as at step 20. Generally, the emulsifier and enteric material can be added to the water together or separately, with either being added first. In some cases, the pH of the solution is generally greater than 7, and generally greater than about 7.1 to about 9. In other cases, a base, such as sodium, ammonium or potassium hydroxide, carbonates, bicarbonates and combinations thereof, can be added to the solution to maintain the pH greater than 7, and in yet other cases from greater than 7 to about 9 to maintain dissolution of the enteric polymers in water substantially free of organic solvents.

The functional ingredient is then added to the enteric material solution, such as at step 30. The enteric material solution containing the functional ingredient is then mixed, such as at step 40. In one form, the materials are agitated or mixed to form an emulsion. By one approach, "agitation" or "agitated" generally refers to the use of a top mixer with impeller or a rotor/stator mixing device operating at a speed of less than about 10,000 RPM. Other mixing devices may also be employed.

After mixing, the materials are then acid titrated to precipitate out the functional ingredient microencapsulated with the enteric material, such as at step 50, in a matrix core structure that is generally tiny droplets of functional ingredients substantially homogeneously dispersed in the matrix material. Next, the first coating is applied to the microencapsulated functional ingredient, as shown in step 60. After the first coating is applied, a second coating may be applied, such as shown in step 70. It should be noted that additional coatings may be included beyond the first and second coatings. Optionally, the coatings may include a small amount of a suitable plasticizer, such as one that is soluble/miscible in water.

As shown at step 50, the material is titrated with acid in an amount effective to decrease the pH below the isoelectric or solubility point of the enteric materials causing phase separation and inducing precipitation of the enteric material out of solution with the functional being microencapsulated therein, thus creating a slurry of an aqueous solution and precipitate. The slurry includes a particulate precipitate having a particle size from about 1 to about 1000 micrometers, in some cases about 10 to about 500 micrometers, and in yet other cases from about 75 to about 250 micrometers. In some approaches, precipitation occurs at a pH ranging from about 3 to about 6.5, and in other approaches from about 3 to about 5, and in one approach at a pH of about 4.5. In the method illustrated in FIG. 2, in order to maintain the enteric properties of the particulate precipitate, the fine, stable emulsion of sodium caseinate and soy protein may be titrated with an acid to a pH corresponding to the insolubility at the isoelectric point of sodium caseinate, such as about 4.4 to about 4.6. In some approaches, the slurry may be allowed to settle, resulting in a clear division of the liquid or supernatant and the settled particulate.

While not wishing to be limited by theory, it is believed that as the pH of the emulsion drops below the solubility point, enteric materials, such as soy protein and sodium caseinate may cross-link to like particles or to one another to form a matrix, the hydrophobic liquid being microencapsulated within the matrix. As a result of the cross-linking, the functional ingredient is homogeneously dispersed throughout the matrix. The matrix further provides a seal for the functional ingredient. As a result, the impact of the functional ingredient on the organoleptic qualities of the finished product is generally correlated to any functional ingredient remaining adhered to the outer surface of the enteric material that is not coated.

The acid used for step 50 can be any acid, including, but not limited to, food grade acid. In one approach, the acid is a weak food grade acid. For example, the acid may be citric acid.

As noted above, the composition of the enteric material affects the dissolution rate and the protection provided by the enteric matrix. As a result, the rate and amount of acid addition varies based on the enteric matrix materials used.

To reclaim the precipitate, the slurry may be optionally filtered to produce a wet cake, then washed and dried to produce a dried cake. In some approaches, the particulate and the supernatant are both filtered to produce a cake, then washed and dried to provide a dried cake. In another approach, the slurry or supernatant and particulate are filtered to provide a wet cake. The wet cake is then washed, refiltered and rewashed prior to drying. In some approaches, the surface oil on the outer surface of the particulate precipitate is less than about 1 percent by weight of the final product.

Each solution to prepare the first and second outer coatings can include about 5 percent to about 20 percent enteric material and about 1 percent to about 3 percent plasticizer including, but not limited to, glycerin and other suitable plasticizers. The final, coated microencapsulated particles can include between about 1 to about 15 percent by weight of each of the first and second coatings.

The coating materials can be applied to the enteric matrix by mixing, spraying or other suitable application. In one approach, the coating materials are first solubilized in water. A base can optionally be added to the solubilized outer coating material to increase the pH to greater than 7, in some cases between about 7.1 and about 12. The solubilized material can then be atomized and sprayed onto the uncoated particulate product.

In some instances, the first and second coatings each have coating thicknesses of about 1 micrometer to about 5 micrometers. If desired, the coated matrix particles can then be sieved to meet the desired particle size.

Additional processing steps after the second coating may also be included. For example, such steps may include drying and/or otherwise removing moisture from the coated microcapsules to form a material having less than about 10%, and, in some forms, less than 5% moisture.

In one instance, the coating materials are applied by spraying a fine mist of the respective coating onto fluidized core capsules to create a uniform particle coating. Such a process can include top and/or bottom spraying. In one form, such a process can combine simultaneous layer coating with instant drying.

Other steps may also be included, such as grinding the dried material to form a powder. Further, other intermediate steps may also be included in the process. For example, such steps may include, but are not limited to, washing the microencapsulated material to remove unencapsulated functional ingredients, pH adjustments and the like. In one embodiment, a surface oil remover may be added to aid in removing residual surface oil from the precipitate, as described in co-pending application Ser. No. 12/479,433, filed Jun. 5, 2009, which is incorporated herein in its entirety by reference. Further, the surface oil remover can also be added at any point in the preparation after acid titrating.

Further, the powder can be pulverized to reduce the particle size of the powder precipitate, and then further dried to a moisture content of less than about 5 percent, such as with a fluidized bed dryer. By one approach, the resultant particles have a particle size ranging from about 1 to about 1000 micrometers, in some approaches from about 10 to about 500 micrometers, and in other approaches from about 75 to about 250 micrometers.

When drying the powder, the temperature may be maintained between about 25° C. to about 70° C., in some approaches between about 35° C. to about 60° C., and in other approaches between about 35° C. and about 45° C. During other processing steps, the temperature may be maintained between about 4° C. to about 40° C., in some cases about 4° C. to about 30° C., and in other cases from about 15° C. to about 28° C.

According to one form, the core is substantially free of organic solvents. As used herein, "substantially free of organic solvent" generally refers to an amount of added organic solvent, such as isopropanol or ethanol or any other organic solvent, which is less than the amount of organic solvent required to enable solubilization of the enteric material under the processing conditions. Preferably, the amount of added organic solvent is less than about 0.1 percent by weight of the combination of water, emulsifier and enteric material. As used herein, "organic solvent" generally refers to a non-aqueous, hydrocarbon-based liquid.

The enteric material used herein is any food grade enteric polymer, or a combination or two or more food grade enteric polymers. In one form, the enteric material is a caseinate, such as sodium caseinate, soy protein or a combination thereof.

Other enteric materials that may be included in the core include shellac and zein. The shellac can be provided as an alkaline (pH>7) aqueous solution, such as a water-based solution having a solid content of about 25 percent by weight or it can be prepared from refined, bleached and dewaxed shellac powder. The shellac is substantially free of organic solvent, although it may contain trace amounts of organic solvents, such as isopropyl alcohol (such as can be included in commercial products), to act as a carrier for other ingredients in the shellac solution, such as methyl and propyl parabens. Preferably, the prepared shellac solution does not contain any added organic solvents.

In one approach, the enteric material consists essentially of soy protein and sodium caseinate. It should be noted that soy protein and sodium caseinate may not be thought of as traditional enteric materials. However, when the soy protein and sodium caseinate are prepared near their isoelectric points, the materials take on enteric functionality such that they would be considered enteric materials.

The enteric matrix material and optional emulsifier may be solubilized in water, in one form alkaline water, substantially free of an organic solvent. However, it has been discovered that the combination of the soy protein and sodium caseinate provides an emulsification capability so that the addition of an emulsifier is not required in this approach. Further, the combination of soy protein and sodium caseinate improves stability of the resulting microencapsulated functional ingredient over the duration of the shelf life of the microencapsulated functional ingredient. In one approach, the soy protein and sodium caseinate are solubilized separately in separate aqueous solutions and then combined in a single solution. In some cases, a desired ratio of soy protein to sodium caseinate ranges from about 1:60 to about 60:1 in other cases the ratio ranges from about 1:10 to about 10:1 and in yet other cases the ratio ranges from about 2:1 to about 1:2

The emulsifier described herein is any food grade emulsifier. In one form, the emulsifier is polysorbate, polyglycerol ester, sucrose stearate, sucrose esters, proteins, lecithins or combinations thereof.

The methods described herein combine water, an optional emulsifier, the enteric materials and the functional ingredient in a manner effective to microencapsulate the functional ingredient in the enteric materials. Generally, the methods use water in amounts from about 50 percent to about 95 percent of the combination by weight and, in some approaches, from about 70 to about 95 percent, and, in other approaches, from about 80 to about 90 percent. The optional emulsifier is generally less than about 5 percent of the combination by weight, in some instances from about 0.01 to about 1 percent by weight, and, in other instances, about 0.01 to about 0.1 percent by weight of the combination. The enteric material ranges from about 3 percent to about 35 percent by weight, in some approaches from about 3 to about 23 percent, and, in other approaches, from about 10 percent to about 15 percent by weight of the combination. The functional ingredient generally is in amounts of about 1 to about 15 percent by weight of the combination, and in other approaches, about 3 to about 6 percent by weight, as measured in a wet state prior to titration.

The microencapsulated hydrophobic liquid produced by the above described methods may have an increased payload. Payload generally refers to the weight percentage of the functional ingredients in relation to the final particulate product. The total payload generally refers to the total weight percentage of all the encapsulated functional ingredients, including the any carrier oil, in relation to the final particulate product. Therefore, an increase in payload corresponds to an increase in functional ingredient per a given amount of enteric matrix.

In one form, the product created by the methods described herein may be used for delivery in a powdered soft drink (PSD) beverage. Further, the product created by the methods described herein may be used in a variety of other drinks, such as hot beverages, including, but not limited to, tea, coffee, hot chocolate, and other hot beverages. Other exemplary uses of the product include other food products, such as biscuits, bars, snacks, instant meals and the like.

Advantages and embodiments of the methods described herein are further illustrated by the following Examples. However, the particular conditions, processing schemes, materials, and amounts thereof recited in these Examples, as well as other conditions and details, should not be contrasted to unduly limit this method. All percentages are by weight unless otherwise indicated.

EXAMPLES

Example 1

This Example illustrates one method of preparing microcapsules stable in a hot beverage at temperature of up to 70° C. The core microcapsules are prepared with a 1:1 combination of soy and caseinate proteins. The core material was prepared as found below in Table 1.

TABLE 1

Summary of enteric ingredients in core composition.

| Ingredients | Amount |
| --- | --- |
| RO Water | 7300 g |
| Soy Protein Isolate | 350 g |
| Sodium Caseinate | 350 g |

Initially, the soy protein and sodium caseinate powder were added to water with overhead mixing. The powders were added slowly with the mixing gradually increasing from low to high speed. Low speed was used initially to avoid excess foaming. The materials were mixed for approximately 30 minutes.

Next, 5% NaOH solution was added slowly while mixing until the mixture reaches a pH of approximately 9.0. The conditions for the step are as follows: initial pH: 6.90; final pH: 8.99; amount of 5% NaOH=295.0 g.

Next, approximately 240 g of an essential oil blend was added slowly to the vortex. The essential oil blend included the following composition 10 wt. % para-cymene, 5 wt. % alpha-pinene, 15 wt. % linalyl acetate, and about 70 wt. % thymyl octanoate. The material was left to mix for 5 minutes. Therefore, the mixture contained a ratio of about 2.91:1 of the enteric materials (soy protein and sodium caseinate) relative to the essential oil blend.

After mixing, the composition was homogenized at 500/5000 psi in a two-stage homogenizer. Before homogenizing the mass was approximately 8462.0 g while after homogenizing the mass was approximately 8374.2 g.

After homogenizing, the material was titrated with 12% citric acid solution to pH 4.5. The material was then left to mix for 5-10 minutes. The conditions for this step are as follows: initial pH: 8.86; final pH: 4.50; amount of 12% citric acid solution=545.2 g.

After titrating with acid, the material is dewatered by pressing the precipitate at 40 psi for 30 minutes. Next, the pressed cake is ground using food processor and then spread in a fluid bed drier to dry at approximately 60° C. The initial moisture prior to drying was 53.12%. After drying in the fluid bed drier for about 1 hour, the moisture content was below 5%. Final moisture: 3.74%.

Next, the dried material is finely ground. The ground material was then sifted to collect a fraction between 100-250 μm. The materials was reground and resifted.

After grinding, the material is coated. Two layers of coating were applied to the microcapsules. The first coat was zein, and the second coat was ethylcellulose. Coating was performed in a bench mini-Glatt fluid bed coater with a Wuster insert and bottom spray. The compositions of the coatings are shown below in Tables 2 and 3.

TABLE 2

| Zein coating - Coating solution at 10% zein | |
| --- | --- |
| Ethanol 200 proof | 157.5 g |
| DI Water | 67.5 g |
| Zein Powder | 25 g |
| Total | 250 g |

TABLE 3

| Ethylcellulose coating - Coating solution at 8.33% EC: | |
| --- | --- |
| Ethanol 200 proof | 247.5 g |
| DI Water | 27.5 g |
| EC 4 Standard | 12.5 g |
| EC 10 Standard | 12.5 g |
| Total | 300 g |

As shown above, EC 4 and EC 10 refer to the viscosities of the respective ethylcellulose materials. For example, when hydrated in a solvent at room temperature, EC 4 has a viscosity of 4 cps while EC 10 has a viscosity of 10 cps. In one form, the viscosity and molecular weight may play a role in the processability and/or functionality. Lower viscosity (lower molecular weight) allows the preparation of high concentrations of coating solutions where the high molecular weight provides a better functionality. Combining the two may allow for achieving both results.

For coating, 200 g of the core capsules were loaded into a Mini-Glatt fluid bed coater with a Wurster insert. The powder was fluidized at 0.1-0.3 Bar. Inlet temperature was set at 60° C. Once the product was warmed up to target temperature of about 30-35° C., the coating material was pumped in at a pump speed of 9 (about 1.2-2.0 ml/minute), and nozzle atomization pressure set to 1.5 bars. Coating continued until all of coating solution was applied to achieve 10% for each of the coatings on dry weight basis. At the end, the powder was cooled to ambient temperature and collected for further evaluation.

Example 2

Example 2 was prepared to compare a core material prepared with just sodium caseinate and not including soy protein in a pilot plant. Approximately 89060 g of RO water was used to hydrate 8540 g of sodium caseinate powder. In a vacushear vessel, water was loaded and a vacuum was pulled to maintain the mixing under negative pressure (vacuum) to minimize foaming of the caseinate solution. The caseinate powder was suctioned in slowly while mixing using an overhead mixer. Mixing continued under vacuum until all of caseinate powder was hydrated. Mixing continued for extra 10 minutes. Caseinate solution was transferred into an open tank using an overhead mixer.

Next, 2928 g of an essential oil blend including 10 wt. % para-cymene, 5 wt. % alpha-pinene, 15 wt. % linalyl acetate, and about 70 wt. % thymyl octanoate was added slowly to the mixing caseinate solution to create a coarse emulsion. Once complete, the coarse emulsion was pumped through a single stage high pressure homogenizer at 8000 psi. A fine emulsion was collected in an open tank using an overhead mixer. Therefore, the mixture contained a ratio of about 2.91:1 of the enteric materials (sodium caseinate) relative to the essential oil blend.

Next, acid titration was performed using 12% citric acid which was pumped into the tank with mixing until solution reached a pH of 4.5. At this pH, the caseinate precipitated out with the essential oils entrapped within the enteric material, forming a slurry.

The formed slurry was filtered by using a filter bag at 40 psi and the filter cake was collected for further processing. Next, the cake was coarse ground using a Fitz mill, and then loaded into a Uni-Glatt fluid bed dryer. The coarse ground material was dried to a moisture below 5% in the fluid bed drier.

The dried powder was reground using a Hammer Mill (Bourmister), then collected powder was sifted and product in the range of 75-250 μm was collected, and large size material was re-ground and sifted again. The finely ground material was then coated as per Example 1.

Example 3

Example 3 was prepared to compare a core material prepared with just soy protein and not including sodium caseinate. The composition of the core is provided in Table 4 below.

TABLE 4

Summary of enteric components in core composition.

| Ingredients | Amount |
|---|---|
| RO Water | 7300 g |
| Soy protein | 700 g |

Soy powder was hydrated in water with overhead mixing with the soy powder being added slowly, starting with low to high speed. The composition was allowed to mix for 30 minutes. Next, 5% NaOH solution was added slowly while mixing to pH 9.0. Final pH: 8.99; Amount of 5% NaOH=184.5 g. The functional ingredient was added next with 240 g of an essential oil blend including 10 wt. % para-cymene, 5 wt. % alpha-pinene, 15 wt. % linalyl acetate, and about 70 wt. % thymyl octanoate, being added to the vortex. The solution was left to mix for 5 minutes. The solution was then homogenized at 500/5000 psi. Therefore, the mixture contained a ratio of about 2.91:1 of the enteric materials (soy protein) relative to the essential oil blend.

Next, the homogenized solution was titrated with 12% citric acid solution to pH 4.5 and left to mix for 5-10 minutes. Final pH: 4.54; Amount of 12% citric acid solution=468.3 g.

The resulting precipitate was dewatered by pressing at 40 psi for 30 minutes. The dewatered material was then coarse ground using a food processor and dried. The initial moisture was 56.64% and the final moisture was less than 5%. The same coatings as in Example 1 were then applied.

Example 4

A similar solution and method as in Example 2 was prepared, except the enteric materials for the core capsules were prepared with a combination of caseinate and shellac (60% caseinate: 40% shellac). Therefore, the mixture contained a ratio of about 2.91:1 of the enteric materials (sodium caseinate and shellac) relative to the essential oil blend. The remaining steps were approximately the same with the same coatings as in Example 1.

Figure 3:
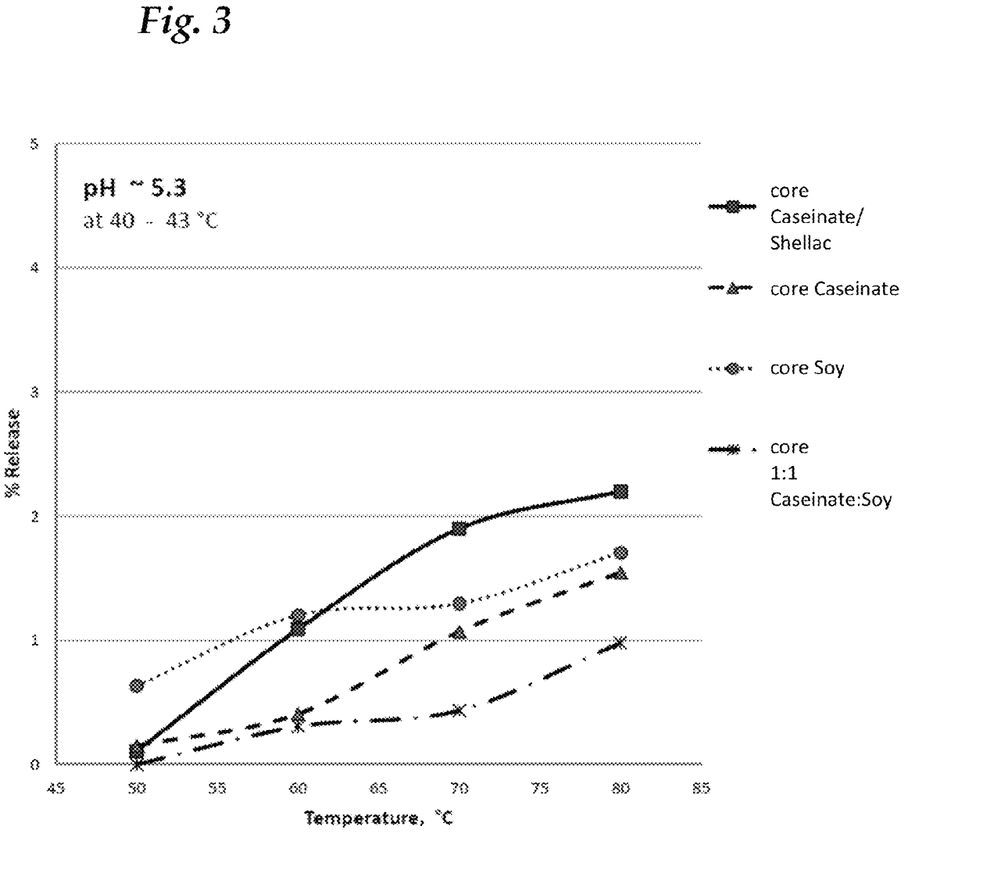
FIG. 3 is a graph illustrating the release of functional components from various core material combinations while at a pH of approximately 5.3.
Figure 4:
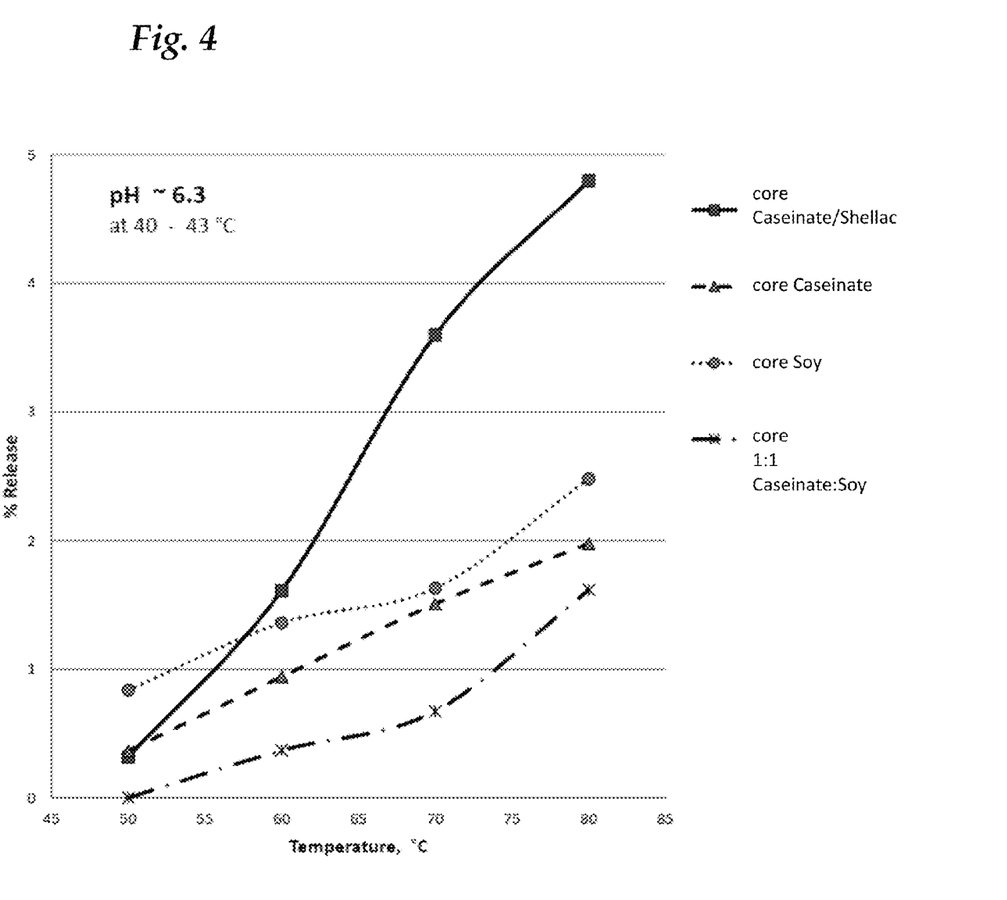
FIG. 4 is a graph illustrating the release of functional components from various core material combinations while at a pH of approximately 6.3.

Referring to FIGS. 3-4, the compositions from Examples 1-4 were compared at various pH levels to show the release profiles of the contained functional ingredients. As seen in FIGS. 3 and 4, Example 1, prepared with both soy protein and sodium caseinate in the core had significantly improved performance compared to soy protein alone, sodium caseinate alone and sodium caseinate with shellac. Better performance is shown by a lower % release of the functional ingredient. It should be noted that the total amount of enteric materials in the respective cores were the same. In other words, the total loading of sodium caseinate and soy protein in Example 1 was equivalent to the sodium caseinate in Example 2, the soy protein in Example 3 and the sodium caseinate and shellac in Example 4.

As seen in FIGS. 3 and 4, both of the examples with just soy protein or just sodium caseinate had inferior performance compared to the sample with sodium caseinate and soy protein. This was unexpected as the performance of the combination of soy protein and sodium caseinate would not be expected to be any better than the equivalent loading of the best performing of the two components when used separately. In other words, sodium caseinate, when used at the set loading, had improved performance compared to soy protein at the same loading and it is unexpected that by replacing a portion of the better performing sodium caseinate with the inferior performing soy protein, the resulting combination had improved performance over more of both components when used individually.

Example 5

Example 5 was prepared to evaluate compositions prepared in a hot beverage. A powdered chocolate type beverage was used as the main beverage material. Water was heated to boil, and then 200 ml was poured into a glass. 20 g of the powdered chocolate beverage was mixed in. Microcapsules prepared according to Examples 1-4 were each dry blended with sugar (about 0.5 capsules and 4.5 g sugar). The capsules/sugar blend was added to chocolate beverage at different temperatures to compare any effect temperature may have. The hot beverage was allowed to cool down to drinkable temperature (about 40° C.), and taste and analyzed. The preparation was done at two different pH conditions of pH 6.3, and lower pH of 5.3 through the addition of lactic acid.

The amount of essential oil released into the beverage correlates with taste. The higher the amount of essential oil released, the stronger the off taste. It is believed that the taste threshold is estimated at a range of 0.5-1.0%. Release was significantly lower at pH 5.3 than at pH 6.3. Of the microcapsules used, the best results were achieved with the soy and caseinate core combination which showed significantly lower release, even at 70° C. Further, in an informal panel, it was concluded that the product prepared with capsules from Example 1, soy and sodium caseinate, provided the cleanest taste profile. No objectionable off-tastes or flavors were noted.

Example 6

The samples from Examples 1-4 were prepared and used in an in vitro digestion model for Example 6 to determine their enteric performance. Capsules were first incubated in gastric juices for 30 minutes, and then in intestinal fluids for 24 hours. Analysis of % release of the functional ingredients was carried out at 30 minutes for the gastric release, 30 minutes post gastric, and then every 2 hours in intestinal fluid for up to 6 hours, and then at 24 hours.

Figure 5:
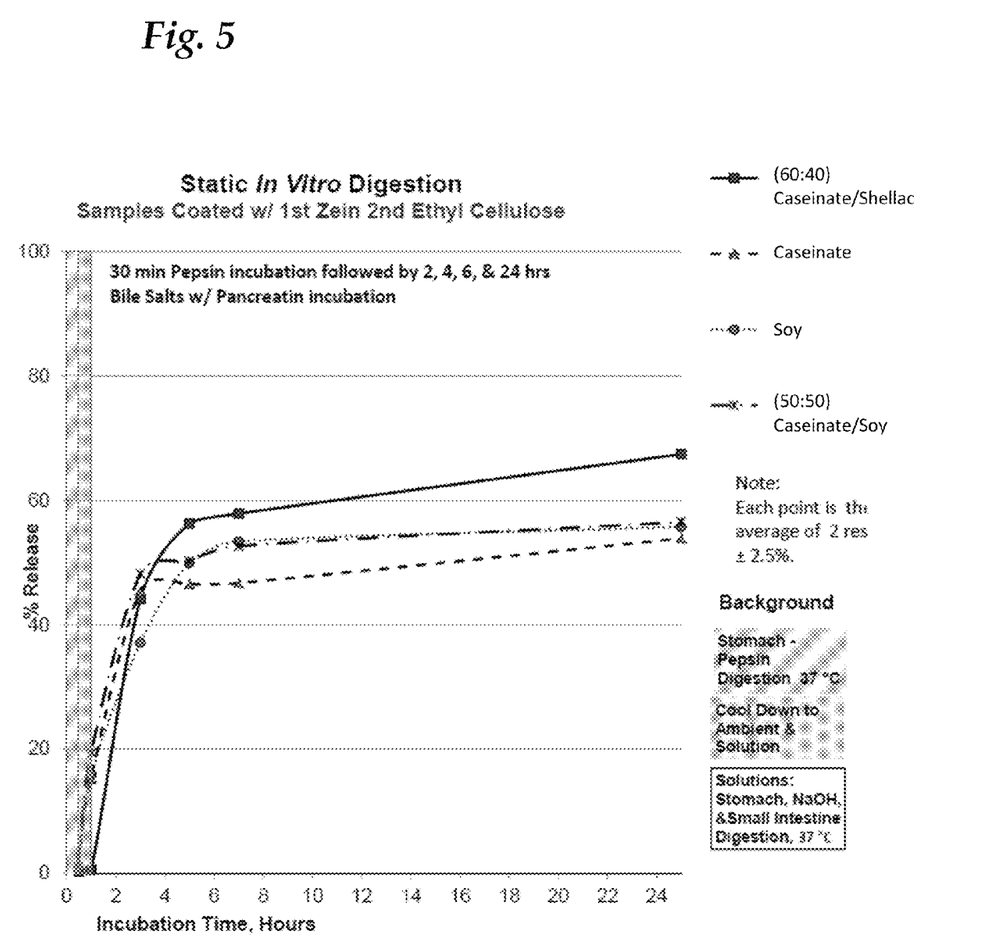
FIG. 5 is a graph illustrating in vitro digestion and release of functional components from various core material combinations over time.

The results are illustrated in FIG. 5. As found in FIG. 5, the sodium caseinate and soy protein core provided suitable release during digestion. After the composition is initially ingested, the material passes through the stomach and eventually on to the intestines, where it is desired that the enteric material release the functional ingredient for delivery. Therefore, the overall composition should provide protection during ingestion and when in the stomach, having a lower release of the functional ingredients as shown in FIGS. 3 and 4, but should also provide proper release of the functional ingredients in the intestines, as found in FIG. 5. Therefore, as found in FIGS. 3-5, Example 1, prepared with soy protein and sodium caseinate in the core, had improved performance and a lower release during preparation of the comestible and ingestion while maintaining the desired release characteristics in the intestines.

While the compositions and methods have been particularly described with specific reference to particular process and product embodiments, it will be appreciated that various alterations, modifications, and adaptations may be based on the present disclosure, and are intended to be within the spirit of this disclosure.

What is claimed is:

1. A microencapsulated composition for use in hot foods and beverages, the composition comprising:
   a core including a functional ingredient and an enteric material to microencapsulate the functional ingredient within a matrix of the enteric material, the enteric material including sodium caseinate and soy protein;
   a first coating substantially surrounding the core, the first coating including zein; and
   a second coating substantially surrounding the first coating, the second coating including ethylcellulose.

2. The microencapsulated composition of claim 1 wherein the enteric material consists essentially of sodium caseinate and soy protein.

3. The microencapsulated composition of claim 1 wherein the core includes about 1 to about 80 wt. % of sodium caseinate and about 1 to about 80 wt. % soy protein, each on a dry basis of the core.

4. The microencapsulated composition of claim 1 wherein the composition has a moisture content of less than about 5 wt. %.

5. The microencapsulated composition of claim 4 wherein the composition comprises about 1 to about 70 wt. % sodium caseinate and about 1 to about 70 wt. % soy protein, each on a dry basis of the total composition.

6. The microencapsulated composition of claim 1 wherein the composition comprises about 1 to about 19 wt. % zein on a dry basis.

7. The microencapsulated composition of claim 1 wherein the composition comprises about 1 to about 19 wt. % ethylcellulose on a dry basis.

8. The microencapsulated composition of claim 1 wherein the functional ingredient comprises essential oils.

9. A method of forming a multi-coated particulate precipitate of a microencapsulated composition for use in hot foods and beverages, the method comprising:
   agitating a combination of water and an enteric material at an appropriate pH to solubilize the enteric material, the enteric material including soy protein and sodium caseinate;
   adding a functional ingredient to the combination;
   mixing the combination and the functional ingredient to create an emulsion;
   titrating the emulsion with a cross-linking or precipitating agent in an amount effective to form a particulate precipitate including a matrix of the enteric material microencapsulating the functional ingredient;
   coating the particulate precipitate with a first coating including zein to form a coated precipitate; and
   coating the coated precipitate with a second coating including ethylcellulose to form a multi-coated particulate precipitate.

10. The method of claim 9 further comprising the step of drying the particulate precipitate.

11. The method of claim 9 further comprising the step of grinding the particulate precipitate.

12. The method of claim 9 further comprising the step of drying the particulate precipitate to a moisture content of less than about 5%.

13. The method of claim 9 wherein the particulate precipitate includes about 1 to about 70 wt. % sodium caseinate and about 1 to about 70 wt. % soy protein, each on a dry basis of the total composition.

14. The method of claim 9 wherein the multi-coated particulate precipitate includes about 1 to about 19 wt. % zein on a dry basis.

15. The method of claim 9 wherein the multi-coated precipitate includes about 1 to about 19 wt. % ethylcellulose on a dry basis.

16. The method of claim 9 wherein the functional ingredient comprises essential oils.

* * * * *